United States Patent
Ciceron et al.

(10) Patent No.: US 10,125,223 B2
(45) Date of Patent: Nov. 13, 2018

(54) MULTIFUNCTIONAL ACRYLIC OLIGOMERS OF BRANCHED STRUCTURE, BY POLYADDITION BETWEEN MULTIFUNCTIONAL AMINES AND ACRYLATES

(71) Applicant: Arkema France, Colombes (FR)

(72) Inventors: Philippe Ciceron, Senlis (FR); Charles Bourrousse, Paris (FR); Catherine M. Leroy, Lille (FR)

(73) Assignee: Arkema France, Colombes (FR)

( * ) Notice: Subject to any disclaimer, the term of this patent is extended or adjusted under 35 U.S.C. 154(b) by 12 days.

(21) Appl. No.: 15/321,023

(22) PCT Filed: Jun. 15, 2015

(86) PCT No.: PCT/FR2015/051575
§ 371 (c)(1),
(2) Date: Dec. 21, 2016

(87) PCT Pub. No.: WO2015/197941
PCT Pub. Date: Dec. 30, 2015

(65) Prior Publication Data
US 2017/0198097 A1 Jul. 13, 2017

(30) Foreign Application Priority Data
Jun. 23, 2014 (FR) .................................. 14 55789

(51) Int. Cl.
| | |
|---|---|
| *C08F 2/46* | (2006.01) |
| *C08F 2/50* | (2006.01) |
| *C08G 61/04* | (2006.01) |
| *C08G 73/06* | (2006.01) |
| *C08F 222/10* | (2006.01) |
| *B33Y 70/00* | (2015.01) |
| *B33Y 80/00* | (2015.01) |
| *C07C 251/08* | (2006.01) |
| *C07D 295/13* | (2006.01) |
| *C08G 73/02* | (2006.01) |
| *C09D 4/00* | (2006.01) |

(52) U.S. Cl.
CPC .......... *C08G 73/0694* (2013.01); *B33Y 70/00* (2014.12); *B33Y 80/00* (2014.12); *C07C 251/08* (2013.01); *C07D 295/13* (2013.01); *C08F 222/1006* (2013.01); *C08G 73/02* (2013.01); *C08F 2222/1013* (2013.01); *C09D 4/00* (2013.01)

(58) Field of Classification Search
CPC .. C08G 73/0694; C08G 73/02; C07D 295/13; B33Y 80/00; B33Y 70/00; C07C 251/08
USPC ........... 522/42, 33, 6, 71, 189, 184, 1; 520/1
See application file for complete search history.

(56) References Cited

U.S. PATENT DOCUMENTS

| | | | | |
|---|---|---|---|---|
| 5,792,827 A * | 8/1998 | Hintze-Bruning | .... | C08F 290/14 428/500 |
| 6,172,129 B1 * | 1/2001 | Fan | ...... | C07D 295/15 252/182.13 |
| 2009/0318611 A1 * | 12/2009 | Bergiers | ................ | C07C 229/30 524/555 |
| 2012/0308734 A1 * | 12/2012 | Deruyttere | ............ | C07C 229/12 427/487 |

FOREIGN PATENT DOCUMENTS

| | | |
|---|---|---|
| EP | 1 876 166 | 1/2008 |
| WO | WO 2011/131501 | 10/2011 |

* cited by examiner

*Primary Examiner* — Jessica Whiteley
(74) *Attorney, Agent, or Firm* — Christopher R. Lewis

(57) ABSTRACT

An acrylated oligomer, having a number-average acrylate functionality $f_o > 2$, of branched structure results from the polyaddition reaction of at least one amine A) having a functionality $f_A$ of N—H groups of at least 2, to at least one multifunctional acrylate B) having a functionality $f_B$ of acrylate groups of at least 2, with an average functionality per mole of all of the components A)+B) of greater than 2 and with the oligomer comprising in its repeating unit structure at least one —O$_2$C—CH$_2$—CH$_2$—N= aminoacrylate group resulting from the polyaddition and with a content of nitrogen resulting from the amine A) of greater than or equal to 0.35 mEq/g and an initial ratio r=acrylate/N—H of between $r_{inf}$ and 1.1 $r_{sup}$ with $r_{inf}=0.90*(f_A-1)*(f_B-1)$ and $r_{sup}=2*f_A+2*f_B-6$ and the average number $n_{av}$ of repeating units per oligomer $n_{av}=1/[(r*f_A/f_B)+1-f_A]$.

25 Claims, No Drawings

# MULTIFUNCTIONAL ACRYLIC OLIGOMERS OF BRANCHED STRUCTURE, BY POLYADDITION BETWEEN MULTIFUNCTIONAL AMINES AND ACRYLATES

CROSS-REFERENCE TO RELATED APPLICATIONS

This application is a U.S. national stage application under 35 U.S.C. § 371 of international application number PCT/FR2015/051575, filed Jun. 15, 2015, which claims priority to French patent application number FR.1455789, filed Jun. 23, 2014.

FIELD OF THE INVENTION

The present invention relates to multifunctional acrylated oligomers having a mean functionality of greater than 2, of branched structure, obtained by polyaddition reaction between a multifunctional amine having an —NH functionality of at least 2 and a multifunctional acrylate having a functionality of at least 2, with an average functionality for the amine and acrylate together of greater than 2, said oligomers resulting from a chain extension by said polyaddition and by the formation in the repeating unit of at least one aminoacrylate group under specific acrylate/N—H molar ratio conditions. Therefore, said oligomers have a controlled structure, obtained by a simple one-step process, having a high reactivity and a controlled viscosity for applications in the fields of coatings or 3D articles made via superposed layers or the field of chemical sealing. The invention also covers a specific process for obtaining said products, a crosslinkable composition comprising them, their uses in the cited applications and the finished products obtained.

The oligomers according to the invention have in particular, as combined advantages, both an acrylate group density per unit of weight and an acrylate group functionality per mole that are higher and better controlled than the comparable products from the prior art, while having a nitrogen content and an aminoacrylate content that are sufficient, in particular for a synergistic effect that activates the UV crosslinking and a low viscosity that is suitable for the targeted applications.

BACKGROUND OF THE INVENTION

Obtaining acrylated aminoacrylates in general, monomers or oligomers, comprising an aminoacrylate group is already known from the prior art and also the performances thereof for a synergistic effect via the presence of the nitrogen atom in the aminoacrylate group for UV crosslinkable compositions. These groups are indeed known for accelerating said crosslinking by participating in a bimolecular initiation mechanism, in the presence of photoinitiators such as benzophenone, via the electron donor effect of the nitrogen atom which renders labile the hydrogens at the a position of the tertiary amine function.

U.S. Pat. No. 6,172,129 describes in particular aminoacrylates resulting from the addition of cyclic secondary monoamines to a multifunctional acrylate having at least 3 acrylate groups per molecule. These products do not comprise any possible chain extension and have a monomeric structure, with in particular a reduction of the functionality of the final product with respect to the initial multifunctional acrylate and they therefore have a lower density of acrylate groups per unit of weight than said initial multifunctional acrylate, despite their low viscosity. These products, in order to reach a high content of aminoacrylate groups, contain a high proportion of saturated species resulting from the addition of a secondary monoamine to all of the acrylate groups of the initial multifunctional acrylate.

WO 2011/131501 describes amino(meth)acrylates obtained by addition reaction of an amine with a mixture of urethane(meth)acrylates and a (meth)acrylated reactive diluent. These products have, in their structure, a chain extension by aminoacrylate groups generated by polyaddition between a primary amine or a secondary diamine and said multifunctional urethane(meth)acrylate. However, they have the drawback of having high viscosities, even in the presence of a reactive diluent, firstly due to the nature of the multifunctional (meth)acrylic monomers which are urethanes and then due to the absence of strict control of this extension and of the final structure. This is without considering the fact that the methacrylate groups, cited as an alternative possibility to the acrylates, cannot give a polyaddition reaction with an amine (insufficiency of description with non-feasibility of a portion of the structures described). Moreover, the density of residual acrylate groups is lower than that of the initial multifunctional acrylate with a higher final viscosity.

SUMMARY OF THE INVENTION

The present invention finds a solution to the cited prior art drawbacks by proposing novel multifunctional acrylated oligomers that at the same time have a higher functionality of acrylate groups than that of the starting multifunctional acrylate due to the effect of the presence of acrylate groups at the chain ends and in the main chain and due to the effect of the branched structure. Specifically these are oligomers comprising aminoacrylate groups with a number-average functionality per oligomer $f_o$>2 acrylates/mole with a high content of nitrogen resulting from the amine $t_A$ ($t_A$>0.35 mEq/g) while having a controlled viscosity that remains <2000 mPa·s at 25° C. according to the ISO 2555 method, without any reactive diluent added. The advantage of such a low viscosity is to avoid the addition of large amounts of reactive diluent. Such products have in particular a high reactivity owing to the combination of their high acrylate functionality $f_o$ and of the synergistic effect of the amine functions, with type I and II initiations possible in the presence of a bimolecular photoinitiator.

In photocrosslinkable formulations, the compromise between crosslinking speed, flexibility, hardness and solvent resistance is improved by the use of such multifunctional acrylated aminoacrylate oligomers.

These aminoacrylates are obtained by polyaddition reaction (referred to as Michael addition or aza addition) of amine A) of functionality $f_A$ ($f_A$: number-average if mixture of amines) of at least 2, to an acrylate B) of functionality $f_B$ of at least 2 ($f_B$ number-average if mixture of acrylates) excluding the case where $f_A=f_B=2$ due to the fact that the number-average functionality of all of the components A) and B) must be greater than 2, thus enabling a controlled branched structure. A "branched" structure means that the oligomer chain obtained comprises at least one chain branching with the same repeating unit. The control of the increase in molecular mass of these systems and therefore of their viscosity is ensured by the ratio r of the number of acrylate double bonds with respect to the number of —NH amine functions (r=Acrylate/NH), the conversion x being greater than 95% with respect to the reactive —NH functions which are fewer in number with respect to the acrylate functions B). The viscosity of such systems remains controllable without leading to the gelation of the reaction medium by the specific limitation of said ratio r which remains greater than a specifically defined value that is dependent on the functionalities of the two components for a given conversion. In all cases, the ratio r=acrylate/NH remains greater than 1 so that the oligomer is acrylated as defined according to the invention.

Among the main advantages of the present invention with respect to the prior art, mention may be made of the following:

For the production process:
  Simple (Aza or Michael) addition reaction of the amine A) to the acrylate B) with a reaction mixture and in a single process step.
  No gaseous effluent or by-products to be eliminated with a yield of 100% with respect to the weight of the reactants.
  No need of solvent or of catalyst, with a reaction temperature of around 80° C. and a short reaction time with a reduced impact on the environment.
  Reproducibility and predictability of the structures and of the final properties on the basis of the criteria of the invention.

For the product:
  Controlled viscosity with a value <2000 mPa·s at 25° C. according to ISO 2555.
  High content of nitrogen $t_A$, resulting from the amine A) with $t_A$ greater than or equal to 0.35 mEq/g.
  Good compromise between number-average acrylate functionality per oligomer, $f_o$ and the density of acrylate groups per unit of weight $t_{acr}$, respectively with $f_o>2$ and $t_{acr}>2.3$ mEq/g.
  Low content of migratables with absence of completely saturated species (absence of complete saturation of the acrylates given the significant excess of acrylate functions with respect to the amine functions).
  Control of the chain lengthening by adjustment of the ratio r=Acrylate/NH and control of the structure without risk of gelation, despite the branching of the chain.

With respect to the applications targeted in radiation-crosslinkable compositions, and in particular UV-crosslinkable compositions, or peroxide-crosslinkable compositions comprising said oligomers of the invention, there are, as advantages, a high reactivity of said oligomers with a high flexibility, hardness and solvent resistance of the crosslinked products obtained.

DETAILED DESCRIPTION OF THE INVENTION

The invention firstly covers the acrylated oligomer of branched structure, as defined according to the invention.

Next, it relates to a specific process for preparing said oligomer.

Another subject relates to a crosslinkable composition comprising said oligomer.

The use of said oligomer in crosslinkable compositions is also part of the invention.

Finally, the invention relates to the crosslinked finished products obtained using said oligomer or a crosslinkable composition containing it.

Therefore, the first subject of the invention relates to an acrylated oligomer, which has a number-average acrylate functionality (or acrylate number-average functionality) $f_o$ of strictly greater than 2 acrylates per mole, which oligomer has a branched structure and results from the polyaddition reaction of at least one amine A) having a functionality $f_A$ of N—H groups of at least 2, preferably of 2 to 6, with said N—H functionality meaning a number-average functionality if it is a mixture of amines, said amine A) bearing primary and/or secondary amine functions, with optionally said amine A) bearing in addition at least one tertiary amine function (i.e. without N—H), with said polyaddition to at least one multifunctional acrylate B) having a functionality $f_B$ of acrylate groups of at least 2, preferably of 2 to 6, with said acrylate functionality $f_B$ meaning a number-average functionality if it is a mixture of acrylates, with a number-average functionality per mole of all of the components A and B of greater than 2 and with said oligomer comprising in its repeating unit structure at least one —O$_2$C—CH$_2$—CH$_2$—N= aminoacrylate group resulting from said polyaddition and with a content of nitrogen $t_A$ resulting from said amine A) of greater than or equal to 0.35 mEq/g and an initial ratio r=acrylate/N—H of between $r_{inf}$ and 1.1 $r_{sup}$, and preferably r between $r_{inf}$ and $r_{sup}$, with the values $r_{inf}$ and $r_{sup}$ being defined according to equations (1) and (2) below:

$$r_{inf}=0.90*(f_A-1)*(f_B-1) \quad (1)$$

$$r_{sup}=2*f_A+2*f_B-6 \quad (2)$$

and with an average number $n_{av}$ of repeating units per oligomer (in addition to the monomer B), defined according to equation (3) below:

$$n_{av}=1/[(r*f_A/f_B)+1-f_A] \quad (3).$$

Said repeating unit corresponds to an aminoacrylate unit, formed by the addition reaction of an NH group of said amine A) to an acrylate group of said multifunctional acrylate B).

According to one particular preference, the sum $f_A+f_B$ remains less than or equal to 8.

More particularly, nay may vary from 0.1 to 5, preferably from 0.15 to 3.

According to a first preferred option, said amine A) additionally bears at least one tertiary amine function, preferably said amine being selected from: dimethylaminopropylamine (DMAPA), dimethylaminopropylaminopropylamine (DMAPAPA) and 1,4-bis(3-aminopropyl)piperazine (1,4-BAPP) and more preferably from DMAPAPA and 1,4-BAPP and with a content of nitrogen to of greater than or equal to 0.35 mEq/g. The content of nitrogen, in this case, includes the nitrogen of all the amine functions, including that of the tertiary amine functions present in this preferred case.

The viscosity of said acrylate B) measured according to the ISO 2555 method at 23° C. is preferably less than 200 mPa·s under a shear of 100 s$^{-1}$. Said acrylate B) is more particularly selected from: b1) optionally alkoxylated aliphatic or cycloaliphatic polyol acrylates, b2) oligoether acrylates, b3) alkoxylated phenolic acrylates or b4) acrylated aminoacrylates or mixtures thereof and preferably b1) or b4) or mixtures thereof. A mixture of acrylates B) may therefore be a mixture of acrylates B) of the same type, that is to say for example a mixture between at least two acrylates of type b1) or of at least two acrylates of type b2) or of at least two acrylates of type b3) or of at least two acrylates of type b4), in particular of at least two acrylates of type b1) or b2) and mixtures between different types thereof.

Said amine A) is preferably selected from: a1) an aliphatic amine, a2) a cycloaliphatic amine or a3) an aralkylene amine with the amine function at a position other than the alpha position (alpha meaning that N is directly bonded to the ring) or other than the beta position (with N borne by a carbon at the alpha position of the aromatic ring) of the aromatic ring or mixtures thereof, preferably a1) aliphatic and/or a2) cycloaliphatic (including polycyclic) amines or mixtures thereof. More specifically, in the particular case a3), the amine function is neither in the alpha position nor in the beta position with respect to the aromatic ring.

Said amine A) may be represented by a general formula $(NH_2)_{fA1}R2(NHR3)_{fA2}$, with $R2=R'(NR''R''')_{fA3}$, R3, R', R'' and R''' being identical or different $C_1$ to $C_3$ alkyls with $f_{A1}$ being the number of primary amine functions per mole, $f_{A2}$ being the number of secondary amine functions per mole and $f_{A3}$ being the number of tertiary amine functions per mole and with $f_A=2*f_{A1}+f_{A2}$.

Said acrylate B) may be represented by the general formula $R1(X)_{fB}$ with X being a $CH_2=CH-CO_2-$ acrylate group and R1 being the residue of said acrylate B) bearing $f_B$ acrylates per mole.

The acrylated oligomer according to the invention has in particular a content of acrylate groups or a density of acrylate groups $t_{acr}$ off greater than 2.3 and preferably of 3.5 to 10 mmol/g or milliequivalents/g (mEq/g).

Said oligomer may be characterized by a calculated number-average molecular mass Mn ranging from 275 to 5000, preferably from 300 to 3000, with Mn being defined according to equation (4) below:

$$M_n=M_B+(n_{av}*M_u) \quad (4)$$

with $M_u$ being the molar mass of the repeating unit defined according to equation (5) below:

$$M_u=M_A+(f_{A2}+2*f_{A1}-1)*M_B \quad (5)$$

$n_{av}$ being the average number of repeating units as defined in claim 1,
$M_B$ being the molar mass of the acrylate B),
$M_A$ being the molar mass of the amine A),
$f_{A1}$ being the number of primary amine —$NH_2$ functions, per amine A) and
$f_{A2}$ being the number of secondary amine —NH— functions, per amine A).

Regarding the content of nitrogen to in said oligomer of the invention, it may vary from 0.4 to 5, preferably from 0.45 to 4 mEq/g, with $t_A$ being defined according to equation (6) below:

$$t_A=1000*n_{av}*(f_{A1}+f_{A2}+f_{A3})/M_n \quad (6)$$

with $M_n$ being the number-average molecular mass as defined above and
$f_{A1}$ being the number of primary amine —$NH_2$ functions, per amine A) and
$f_{A2}$ being the number of secondary amine —NH— functions, per amine A) and
$f_{A3}$ being the number of tertiary amine —N= functions, per amine A).

The functionality fu, expressed in equivalents of (acrylate) double bonds per mole of said oligomer may be defined according to equation (7) below:

$$f_o=f_B+n_{av}*(f_{A2}*f_B-f_{A2}-f_B+2*f_{A1}*f_B-2*f_{A1}) \quad (7)$$

$f_o$ thus defined may vary from 2.1 to 6, preferably from 2.3 to 5.

The acrylate content $t_{acr}$, expressed in milliequivalents (or mmoles) of double bonds per gram of said oligomer, may be defined according to equation (8) below:

$$t_{acr}=1000*f_o/M_n \quad (8)$$

Said acrylate B) may be alkoxylated and in this case preferably the number of alkoxy units per acrylate group does not exceed 3 if said alkoxy is ethoxy and does not exceed 1 if said alkoxy is propoxy.

More particularly, regarding the two reactants A) and B), said amine A) has a functionality $f_A$ greater than or equal to 2 and said acrylate B) has a functionality $f_B$ greater than or equal to 3 or conversely said amine A) has a functionality $f_A$ greater than or equal to 3 and that said acrylate B) has a functionality $f_B$ greater than or equal to 2 and more particularly $f_A+f_B$ does not exceed 8 and preferably less than 8.

According to one particular option where there is an absence of primary amine —$NH_2$ functions in said amine A) ($f_{A1}=0$ in the general formula of amine A)), said oligomer may be defined by the fact that:

said amine A) is of general formula $(NH_2)_{fA1}R2(NHR3)_{fA2}$, with $R2=R'(NR''R''')_{fA3}$, R3, R', R'' and R''' being identical or different $C_1$ to $C_3$ alkyls with $f_{A1}$ being equal to 0 and being the number of primary amine functions per mole, $f_{A2}$ being greater than or equal to 2 and being the number of secondary amine functions per mole and $f_{A3}$ being greater than or equal to 0 and being the number of tertiary amine functions per mole and with $f_A=f_{A2}$ said acrylate B) is of general formula $R1(X)_{fB}$ with X being a $CH_2=CH-CO_2-$ acrylate group and R1 being the residue of said acrylate B) bearing $f_B$ acrylates per mole, and that
said oligomer comprises the product of general formula (I) below:

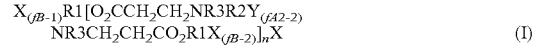

with $Y=-(NR3CH_2CH_2COOR1X_{(fB-1)})$

The more structural and detailed formula of the formula (I) may correspond to the following formula with all the parameters used being defined as above for said formula (I):

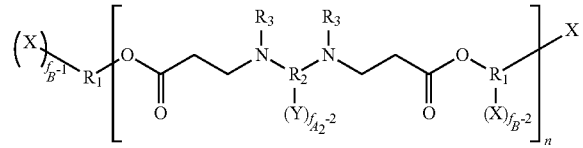

with:

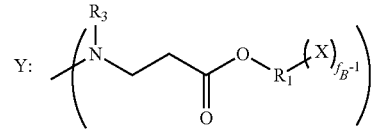

According to another particular option with presence of primary and secondary amine function, said oligomer may be defined by the fact that:

said amine A) is of general formula $(NH_2)_{fA1}R2(NHR3)_{fA2}$, with $R2=R'(NR''R''')_{fA3}$, R3, R', R'' and R''' being identical or different $C_1$ to $C_3$ alkyls, $f_{A1}$ being greater than or equal to 1 and being the number of primary amine functions per mole, $f_{A2}$ being greater than or equal to 0 and being the number of secondary amine functions per mole and $f_{A3}$ being greater than or equal to 0 and being the number of tertiary amine functions per mole and with $$f_A=2*f_{A1}+f_{A2}$$

said acrylate B) is of general formula R1(X)$_{fB}$ with X being a CH$_2$=CH—CO$_2$— acrylate group and R1 being the residue of said acrylate B) bearing $f_B$ acrylates per mole, and that said oligomer comprises the product of general formula (II) below:

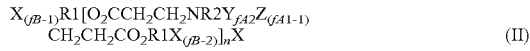

with Y=—(NR3CH$_2$CH$_2$CO$_2$R1X$_{(fB-1)}$ and Z=—(N(CH$_2$CH$_2$COOR1X$_{(fB-1)}$)$_2$).

The more structural and detailed formula of the formula (II) may correspond to the following formula with all the parameters used being defined as above for said formula (II):

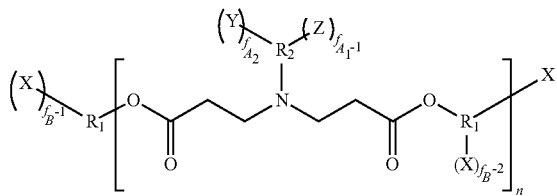

with

Z:

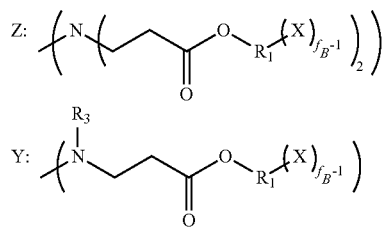

Y:

According to another possibility, said functionality $f_A$ of the amine A) is equal to 3 and said amine A) is selected from a diamine bearing a primary amine function and a secondary amine function or from a triamine bearing 3 secondary amine functions.

According to another variant, said amine A) has a functionality $f_A$ equal to 2 and is a primary amine, i.e. bears a primary amine —NH$_2$ function or is a diamine bearing 2 secondary amine functions and said acrylate B) is an optionally alkoxylated triacrylate with, in the case where said triacrylate is alkoxylated, a number of alkoxy units per acrylate that does not exceed 3 if said alkoxy is ethoxy and a number of alkoxy units per acrylate that does not exceed 1 if said alkoxy is propoxy.

According to another possible variant, said amine A) has a functionality $f_A$ equal to 3 and is a primary-secondary diamine, i.e. bears a primary amine function and a secondary amine function or is a triamine bearing 3 secondary amine functions and said acrylate B) is an optionally alkoxylated diacrylate with, in the case where said diacrylate is alkoxylated, a number of alkoxy units per acrylate that does not exceed 2 if said alkoxy is ethoxy and a number of alkoxy units per acrylate that does not exceed 1 if said alkoxy is propoxy.

According to another option, said functionality $f_A$ of the amine A) is equal to 4 and said amine A) is selected from a diamine bearing 2 primary amine functions or a triamine bearing 1 primary amine function and 2 secondary amine functions or a tetra-amine bearing 4 secondary amine functions.

Again according to a different option, said functionality $f_A$ is equal to 5 and said amine A) is selected from a triamine bearing two primary amine functions and one secondary amine function or a tetra-amine bearing one primary amine function and three secondary amine functions or a penta-amine bearing 5 secondary amine functions.

Again according to another option, said functionality $f_A$ is equal to 6 and said amine A) is selected from a triamine bearing three primary amine functions or a tetra-amine bearing 2 primary amine functions and 2 secondary amine functions or a penta-amine bearing 1 primary amine function and 4 secondary amine functions or a hexa-amine bearing 6 secondary amine functions.

Said amine A) as already mentioned above may be a mixture of primary and/or secondary amines as defined above. In this case, the functionality $f_A$ used is the number average functionality of all the amines used in said mixture. It is possible, according to one particular option, for a monofunctional, in particular cycloaliphatic, secondary amine to be present in said mixture as long as the proportions of the amine components of the mixture and their functionalities of NH groups are such that the number-average functionality $f_A$ of NH groups of said mixture of amines is at least 2 and preferably from 2 to 6.

The oligomer of the invention, of branched structure, has a number-average acrylate functionality fo ranging from 2.1 to 6, preferably from 2.3 to 5 per oligomer, i.e. per mole of oligomer.

According to one particular option, said oligomer may result from the reaction between at least two amines A) and/or at least two acrylates B). This means that it is possible to react, according to the invention, at least two amines A) with at least one acrylate B) or one amine A) with at least two acrylates B) or at least two amines A) with at least two acrylates B).

Said oligomer according to the invention preferably has a number-average molecular mass Mn calculated according to equation (4) defined above ranging from 275 to 5000 and preferably from 300 to 3000 (in g/mol or Dalton).

The oligomer, according to the invention, comprises n repeating units with a molecular distribution as a function of n (number of repeating units), which means that it has a molecular distribution as a function of n and in particular it comprises at least the 4 products corresponding to: n=0 and n=1 and n=2 and n=3 and more particularly with at least 50% by weight of said distribution corresponding to n less than or equal to 3. More particularly, said molecular distribution as a function of n comprises at least the 5 products corresponding to: n=0 and n=1 and n=2 and n=3 and n=4 and more particularly still with at least 60% by weight of said distribution corresponding to n less than or equal to 4.

The second subject of the invention relates to a process for preparing said oligomer as defined according to the invention above, which process comprises a step of polyaddition (addition referred to as Michael addition) reaction of said at least one amine A) to said at least one acrylate B), in the presence of a radical polymerization inhibitor and in the absence of any solvent, of any catalyst and of any other reactant except for said amine A) and said acrylate B) and inhibitor, said process comprising the gradual and continuous addition of said amine A) to said acrylate B) already present in the reactor and B) always in stoichiometric excess and with said reaction taking place at a temperature above 40° C. and below 90° C., preferably from 60° C. to 80° C. and with said reaction being stopped at a degree of conversion of the N—H amine functions of at least 95% and with an initial ratio r of acrylate functions to said N—H amine functions, r=acrylate/N—H being between $r_{inf}$ and 1.1 $r_{sup}$ and preferably r between $r_{inf}$ and $r_{sup}$, with the values $r_{inf}$ and $r_{sup}$ being defined according to equations (1) and (2) below:

$$r_{inf}=0.90*(f_A-1)*(f_B-1) \quad (1)$$

$$r_{sup}=2*f_A+2*f_B-6 \quad (2)$$

Another subject of the invention relates to a crosslinkable composition, which comprises at least one oligomer as defined above or obtained by the process as defined according to the invention, with optionally the presence of a reactive diluent, in particular selected from monofunctional and/or multifunctional (meth)acrylic monomers and with said reactive diluent possibly being identical to said starting acrylate B) or said diluent possibly being different. Said reactive diluent may in particular be used for the highest viscosity values of the range <2000 mPa·s. Said diluent identical to B) is by definition a multifunctional acrylic, like B). If different from B), it may be different due to the nature of the meth(acrylic) functionality, i.e. bearing methacrylate groups or being a monofunctional acrylate or methacrylate or multifunctional (acrylate or methacrylate) having a different nature or a different functionality (acrylate or methacrylate groups per mole) than that of B) (in terms of acrylates). Said reactive diluent, aside from its role of reactive diluent for adjusting the viscosity to that targeted for the final application, may also be used to adjust the final performances of the crosslinked product obtained from said crosslinkable composition.

More particularly, said (crosslinkable) composition is a radiation-crosslinkable composition, preferably that can be crosslinked by UV, laser, LED or EB radiation, which is a coating composition, in particular an ink, varnish, gel coat, paint or adhesive, in particular structural adhesive, composition or is a composition for 3D articles made by superposition of successive layers or is a molding composition.

According to another variant, said composition is a peroxide-crosslinkable composition (commonly referred to as "P-cure" composition) and in particular it is a coating composition, more particularly a varnish, gel coat, paint or adhesive, in particular structural adhesive, composition or is a chemical sealing composition or a molding composition.

The molding compositions are crosslinkable compositions for molded parts and in particular for structural materials, including for composite materials reinforced by fibrous reinforcements.

Another subject of the invention relates to the use of an oligomer as defined above as binder in a crosslinkable composition. According to a first option of said use, said composition is radiation-crosslinkable, preferably that can be crosslinked by UV, laser, LED or EB radiation, said composition being a coating composition, in particular an ink, varnish, gel coat, paint or adhesive, in particular structural adhesive, composition or being a composition for 3D articles made by superposition of successive layers or being a molding composition.

According to another variant of said use, it is of use in a peroxide-crosslinkable composition (commonly referred to as "P-cure" composition) which in particular is a coating composition, more particularly a varnish, gel coat, paint or adhesive, in particular structural adhesive, composition or a chemical sealing composition or a molding composition.

EXAMPLES

Finally, the invention relates to the crosslinked final product which results from the use of at least one oligomer as defined above or obtained by the process defined above or which results from the crosslinking of a composition as defined above according to the invention and in particular which is a coating film, more particularly an ink, varnish, gel coat or adhesive film or a 3D article or a chemical seal or a molded part.

The following examples are given by way of illustration of the invention and of the performances thereof and in no way limit the scope thereof.

Experimental Section

Raw materials: see Table 1 below

TABLE 1

| | raw materials | | | | |
|---|---|---|---|---|---|
| Trade name (REF) | Chemical name | Abbreviated name | Supplier | Function according to the invention | Functionality |
| SR341 | 3-Methyl-1,5-PentaneDiol DiAcrylate | 3M15PDDA | SARTOMER | Acrylate B) | $f_B = 2$ |
| SR238 | HexaneDiol DiAcrylate | HDDA | SARTOMER | Acrylate B) | $f_B = 2$ |
| SR455LM | TriMethylolPropane TetraEthoxylated TriAcrylate | TMP4EOTA | SARTOMER | Acrylate B) | $f_B = 3$ |
| SR454 | TriMethylolPropane TriEthoxylated TriAcrylate | TMP3EOTA | SARTOMER | Acrylate B) | $f_B = 3$ |
| SR351 | TriMethylolPropane TriAcrylate | TMPTA | SARTOMER | Acrylate B) | $f_B = 3$ |
| DMAPA | 3-(DiMethylAmino)-1-PropylAmine | DMAPA | ALDRICH | Amine A) | $f_A = 2$ |
| DMAPAPA | DimethylAminoPropyl-AminoPropylAmine | DMAPAPA | ARKEMA | Amine A) | $f_A = 3$ |
| 1,3BAC | 1,3-Bis(Aminomethyl-Cyclohexane) | 1,3 BAC | MITSUBISHI | Amine A) | $f_A = 4$ |
| 1,4BAPP | 1,4-Bis(3-AminoPropyl)-Piperazine | 1,4 BAPP | ALDRICH | Amine A) | $f_A = 4$ |
| EMHQ | Hydroquinone methyl ether | EMHQ | RHODIA | Inhibitor | |

TABLE 1-continued

| | | | | | |
|---|---|---|---|---|---|
| Trade name (REF) | Chemical name | Abbreviated name | Supplier | Function according to the invention | Functionality |
| Darocure ® 1173 | 2-Hydroxy-2-Methyl-1-PhenylPropan-1-one | Dar1173 | CIBA | Photoinitiator | |
| Benzophenone | DiphenylMethanone | BzPh | ARKEMA | Photoinitiator | |

Examples of Preparation of the Dimmers According to the Invention

Example A1

Introduced into a 1-liter reactor equipped with an anchor agitator and surmounted by a simple ascending condenser, device enabling the venting of the reaction medium, and air inlet (air sparging), a dropping funnel and a temperature probe are: 178.4 g of hexanediol diacrylate (HDDA) (0.7895 mol) and 84.7 mg of hydroquinone methyl ether (EMHQ).

Next, gradually introduced into the reactor via the dropping funnel over one hour are: 33.5 g of dimethylaminopropylaminopropylamine (DMAPAPA) (0.2105 mol) during which the reaction mixture is gradually brought to 80° C. and maintained at this temperature until a conversion of greater than 95% of the primary and secondary (1°+2°) reactive amine functions and stabilisation of the viscosity, i.e. 10 hours of reaction. After cooling to ambient temperature, a product having a clear, light yellow appearance is obtained.

Example A2

Carried out in an identical manner with respect to Example A1, except by replacing, at equal weight for A), the HDDA with 178.4 g of 3-methyl-1,5-pentanediol diacrylate (3M1,5PDDA) (0.7895 mol). A product having a clear, light yellow appearance is obtained.

Example A3

Carried out in an identical manner with respect to Example A1, except that the acrylate B) and amine A) reactants are modified as follows: for B), 188.49 g of dipropyleneglycol diacrylate (DPGDA) (0.7895 mol) and for A), 35.15 g of dimethylaminopropylaminopropylamine (DMAPAPA) (0.2105 mol), A product having a clear, light yellow appearance is obtained.

The molar compositions and characteristics of the 3 oligomers obtained A1, A2 and A3 are presented below in Table 2.

TABLE 2

Molar compositions and characteristics of the oligomers A1, A2 and A3

| Oligomer reference per example | A1 | A2 | A3 |
|---|---|---|---|
| Reactive component (moles) | | | |
| A): 3M1,5PDDA | | 0.7895 | |
| B): DPGDA | | | 0.7895 |
| B): HDDA | 0.7895 | | |
| A): DMAPAPA | 0.2105 | 0.2105 | 0.2105 |

TABLE 2-continued

Molar compositions and characteristics of the oligomers A1, A2 and A3

| Oligomer reference per example | A1 | A2 | A3 |
|---|---|---|---|
| Characteristics | | | |
| r | 2.50 | 2.50 | 2.35 |
| $t_A$ (mEq/g) | 2.94 | 2.94 | 2.69 |
| Viscosity at 25° C. (mPa · s) | 255 | 250 | 590 |
| $t_{acr}$ (mEq/g) | 4.47 | 4.47 | 4.08 |
| $f_o$ (mEq/mol) | 2.57 | 2.57 | 2.57 |
| $n_{av}$ | 0.57 | 0.57 | 0.57 |
| $M_{n\ calc}$ | 575 | 575 | 631 |

Example B1

Carried out in an identical manner with respect to Example A1, except that the acrylate B) and amine A) reactants are modified as follows: for B), 303.45 g of trimethylolpropane (4 ethoxy) triacrylate (TMP4EOTA) (0.6429 mol) and for A), 36.42 g of dimethylaminopropylamine (DMAPA) (0.3571 mol). A product having a clear, light yellow appearance is obtained.

Example B2

Carried out in an identical manner with respect to Example A1, except that the acrylate B) and amine A) reactants are modified as follows: for B), 197.34 g of trimethylolpropane triacrylate (TMPTA) (0.6667 mol) and for A), 34.00 g of dimethylaminopropylamine (DMAPA) (0.3333 mol). A product having a clear, light yellow appearance is obtained.

The table below groups together the molar compositions of the reactants A) and B) and the characteristics of the oligomers B1 and B2 as described above.

TABLE 3

Molar composition of the reactants A) and B) and characteristics of the oligomers B1 and B2

| Oligomer reference | B1 | B2 |
|---|---|---|
| Reactive component (moles) | | |
| B): TMP4EOTA | 0.6429 | |
| B): TMPTA | | 0.6667 |
| A): DMAPA | 0.3571 | 0.3333 |
| Characteristics | | |
| r | 2.70 | 3.00 |
| $t_A$ (mEq/g) | 2.32 | 2.88 |
| Viscosity at 25° C. (mPa · s) | 2000 | 6400 |
| $t_{acr}$ (mEq/g) | 3.57 | 5.76 |
| $f_o$ (mEq/mol) | 4.25 | 4.00 |

TABLE 3-continued

Molar composition of the reactants A) and B) and characteristics of the oligomers B1 and B2

| Oligomer reference | B1 | B2 |
|---|---|---|
| $n_{av}$ | 1.25 | 1.00 |
| $M_{n\ calc}$ | 1190 | 694 |

Example C1

Carried out in an identical manner with respect to Example A1, except that the acrylate B) and amine A) reactants are modified as follows: for B), 193.71 g of hexanediol diacrylate (HDDA) (0.8571 mol) and for A), 28.58 g of 1,4-bis(3-aminopropyl)piperazine (1,4BAPP) (0.1429 mol). A product having a clear, light yellow appearance is obtained.

The molar composition of the reactants A) and B) and characteristics of the oligomers D1 and D2 are presented in Table 5 below.

Example C2

Carried out in an identical manner with respect to Example A1, except that the acrylate B) and amine A) reactants are modified as follows: for B), 193.71 g of hexanediol diacrylate (HDDA) (0.8571 mol) and for A), 20.29 g of 1,3-bis(aminomethyl)cyclohexane (1,3BAC) (0.1429 mol). A product having a clear, light yellow appearance is obtained.

The molar composition of the reactants A) and B) and characteristics of the oligomers C1 and C2 are presented in Table 4 below.

TABLE 4

Molar composition of the reactants A) and B) and characteristics of the oligomers C1 and C2

| Oligomer reference | C1 | C2 |
|---|---|---|
| Reactive component (moles) | | |
| B): HDDA | 0.8571 | 0.8571 |
| A): 1,3BAC | | 0.1429 |
| A): 1,4BAPP | 0.1429 | |
| Characteristics | | |
| r | 3.00 | 3.00 |
| $t_A$ (mEq/g) | 2.57 | 1.34 |
| Viscosity at 25° C. (mPa · s) | 955 | 340 |
| $t_{acr}$ (mEq/g) | 5.14 | 5.34 |
| $f_o$ (mEq/mol) | 2.67 | 2.67 |
| $n_{av}$ | 0.33 | 0.33 |
| $M_{n\ calc}$ | 519 | 499 |

Example D1

Carried out in an identical manner with respect to Example A1, except that the acrylate B) and amine A) reactants are modified as follows: for B), 380.45 g of trimethylolpropane (3 ethoxy) triacrylate (TMP3EOTA) (0.8889 mol) and for A), 22.22 g of 1,4-bis(3-aminopropyl)piperazine (1,4BAPP) (0.1111 mol). A product having a clear, light yellow appearance is obtained.

Example D2

Carried out in an identical manner with respect to Example A1, except that the acrylate B) and amine A) reactants are modified as follows: for B), 380.49 g of trimethylolpropane (3 ethoxy) triacrylate (TMP3EOTA) (0.8889 mol) and for A), 15.78 g of 1,3-bis(aminomethyl)cyclohexane (1,3BAC) (0.1111 mol). A product having a clear, light yellow appearance is obtained.

The molar composition of the reactants A) and B) and characteristics of the oligomers D1 and D2 are presented in Table 5 below.

TABLE 5

Molar composition and characteristics of the oligomers D1 and D2

| Oligomer reference | D1 | D2 |
|---|---|---|
| Reactive component (moles) | | |
| TMP3EOTA | 0.8889 | 0.8889 |
| 1,3BAC | | 0.1111 |
| 1,4BAPP | 0.1111 | |
| Characteristics | | |
| r | 6.00 | 6.00 |
| $t_A$ (mEq/g) | 1.10 | 0.56 |
| Viscosity at 25° C. (mPa · s) | 1740 | 1278 |
| $t_{acr}$ (mEq/g) | 5.52 | 5.61 |
| $f_o$ (mEq/mol) | 4.00 | 4.00 |
| $n_{av}$ | 0.20 | 0.20 |
| $M_{n\ calc}$ | 725 | 713 |

The oligomers prepared according to the examples described above were tested in crosslinkable formulations (application compositions) as described below.

Formulations and Preparation

The oligomers are formulated by mixing at ambient temperature according to the following compositions F1 to F18 with two types of formulations tested.

Odd Formulae (F1, F3, F5, . . . F17)
Acrylate oligomer (A1 to D2): 96% by weight
Darocure® 1173: 4% by weight
Even Formulae (F2, F4, F6, . . . F18)
Acrylate oligomer (A1 to D2): 96% by weight
Darocure® 1173: 2% by weight
Benzophenone: 2% by weight The compositions of the formulations produced F1 to F18 and their performances are presented in Tables 6 to 9 below. The methods of characterizing said oligomers and of determining the performances of said formulations F1 to F18 and the conditions used are mentioned below after these Tables 6 to 9.

TABLE 6

Formulations F1 to F6 based on oligomers A1 to A3

| | Formulation reference | | | | | |
|---|---|---|---|---|---|---|
| | F1 | F2 | F3 | F4 | F5 | F6 |
| Components | | | | | | |
| A1 | 96.0 | 96.0 | | | | |
| A2 | | | 96.0 | 96.0 | | |
| A3 | | | | | 96.0 | 96.0 |
| Darocure ® 1173 | 4.0 | 2.0 | 4.0 | 2.0 | 4.0 | 2.0 |
| Benzophenone | | 2.0 | | 2.0 | | 2.0 |

TABLE 6-continued

Formulations F1 to F6 based on oligomers A1 to A3

| | Formulation reference | | | | | |
|---|---|---|---|---|---|---|
| | F1 | F2 | F3 | F4 | F5 | F6 |
| Performances | | | | | | |
| Crosslinking speed (mm/min) | 25 | 55 | 20 | 55 | 25 | 60 |
| Persoz hardness | 91 | 139 | 84 | 114 | 59 | 75 |
| Pencil hardness (5B-5H) | H | H | HB | HB | B | HB |
| Flexibility (mm) | 3 | 3 | 3 | 3 | 4 | 3 |
| Solvent resistance (s) | 300 | 300 | 300 | 300 | 54 | 126 |

TABLE 7

Formulations F7 to F10 based on oligomers B1 and B2

| | Formulation reference | | | |
|---|---|---|---|---|
| | F7 | F8 | F9 | F10 |
| Components | | | | |
| B1 | 96.0 | 96.0 | | |
| B2 | | | 96.0 | 96.0 |
| Darocure ® 1173 | 4.0 | 2.0 | 4.0 | 2.0 |
| Benzophenone | | 2.0 | | 2.0 |
| Performances | | | | |
| Crosslinking speed (mm/min) | 40 | 65 | 100 | |
| Persoz hardness | 96 | 157 | 97 | |
| Pencil hardness (5B-5H) | HB | HB | 4B | |
| Flexibility (mm) | 4 | 4 | 20 | |
| Solvent resistance (s) | 300 | 300 | 300 | |

TABLE 8

Formulations F11 to F14 based on oligomers C1 and C2

| | Formulation reference | | | |
|---|---|---|---|---|
| | F11 | F12 | F13 | F14 |
| Components | | | | |
| C1 | 96.0 | 96.0 | | |
| C2 | | | 96.0 | 96.0 |
| Darocure ® 1173 | 4.0 | 2.0 | 4.0 | 2.0 |
| Benzophenone | | 2.0 | | 2.0 |
| Performances | | | | |
| Crosslinking speed (mm/min) | 35 | 65 | 30 | 45 |
| Persoz hardness | 94 | 93 | 113 | 91 |
| Pencil hardness (5B-5H) | 2H | H | HB | HB |
| Flexibility (mm) | 6 | 4 | 8 | 6 |
| Solvent resistance (s) | 300 | 300 | 300 | 300 |

TABLE 9

Formulations F15 to F18 based on oligomers D1 and D2

| | Formulation reference | | | |
|---|---|---|---|---|
| | F15 | F16 | F17 | F18 |
| Components | | | | |
| D1 | 96.6 | 96.0 | | |
| D2 | | | 96.0 | 96.0 |
| Darocure ® 1173 | 4.0 | 2.0 | 4.0 | 2.0 |
| Benzophenone | | 2.0 | | 2.0 |
| Performances | | | | |
| Crosslinking speed (mm/min) | 35 | 55 | 25 | 40 |
| Persoz hardness | 160 | 124 | 186 | 170 |
| Pencil hardness (5B-5H) | 3H | B | HB | HB |
| Flexibility (mm) | 15 | 10 | 20 | 15 |
| Solvent resistance (s) | 300 | 300 | 300 | 300 |

Methods of Determining the Characteristics of the Oligomers the Performance of the Formulations 1) Appearance The product is observed visually in daylight through a 60 ml colorless glass flask and it is distinguished whether the product is:

clear: no turbidity, it is comparable to water, hazy: no longer enabling clear vision through the flask, cloudy: opaque flask, no image can be seen through the flask.

2) Viscosity according to Noury viscosity

The time of travel, in the liquid to be characterized, of a steel ball subjected to its own gravity is measured. The AFNOR XP.T51-213 standard specifies in particular the geometry of the container, the diameter of the ball (2 mm) and the course of the ball (104 mm). Under these conditions, the dynamic viscosity is proportional to the travel time of the ball with: 1 second corresponding to 0.1 Pa·s.

3) Content of amine $t_A$: Calculation according to equation (6) defined above in the description 4) Functionality $f_o$: Calculation according to equation (7) define above in the description 5) Content of acrylate $t_{acr}$: Calculation according to equation (8) defined above in the description 6) Reactivity through crosslinking speed The formulations F1 to F18 are applied as a 12 μm film to a contrast card (Leneta "Penoparc charts form 1B"®), then crosslinked using a 120 W/cm Hg Fusion UV lamp. The minimum run speed needed (in m/min) to obtain a film that is dry to the touch is measured. The higher the speed, the more reactive the formulation.

For the hardness, flexibility and acetone resistance tests, the photocrosslinked films are left in an air-conditioned room at 23° C. for 24 hours after crosslinking and before the measurements.

7) Persoz hardness

The formulation to be examined is applied as a 100 μm film to a glass plate and crosslinked using a 120 W/cm Hg Fusion UV lamp at a speed of 8 m/min.

The result is given as the number of oscillations before damping of the oscillations (passing from an amplitude of 12° to 4°), of a pendulum in contact with the coated glass plate, according to the ISO 1522 standard.

8) Flexibility

The formulation examined is applied as a 100 μm film to a smooth steel plate having a thickness of 25/10 mm (D-46® Q-Panel), then crosslinked using a 120 W/cm Hg Fusion UV lamp at a speed of 8 m/min.

The coated plate is bent round cylindrical mandrels, according to the ISO 1519 standard. The result is expressed by the value (in mm) of the smallest radius of curvature that can be imposed on the coating without it cracking or detaching from the support.

9) Acetone resistance (chemical resistance)

The formulation examined is applied as a 12 μm film to a glass plate, then crosslinked using a 120 W/cm Hg Fusion UV lamp at a speed of 8 m/min. The coating is rubbed with a cloth soaked in acetone. The result used corresponds to the time (expressed in seconds) beyond which the film detaches and/or disintegrates.

10) Number-average molecular mass Mn: Calculation according to equation (4) defined above in the description.

The invention claimed is:

1. An acrylated oligomer, wherein the oligomer has a number-average acrylate functionality $f_o$ of greater than 2 acrylates per mole, has a branched structure and results from the polyaddition reaction of at least one amine A) having a functionality $f_A$ of N—H groups of at least 2, with said N—H functionality meaning a number-average functionality if it is a mixture of amines, said amine A) bearing primary and/or secondary amine functions, with said amine A) bearing at least one tertiary amine function (without N—H) and of at least one multifunctional acrylate B) having a functionality $f_B$ of acrylate groups of at least 2, with said acrylate functionality meaning a number-average functionality if it is a mixture of acrylates, with a number-average functionality per mole of all of the components A) and B) of greater than 2 and with said oligomer comprising in its repeating unit structure at least one —$O_2C$—$CH_2$—$CH_2$—N= aminoacrylate group resulting from said polyaddition and with a content of nitrogen $t_A$, resulting from said amine A), of greater than or equal to 0.35 mEq/g and an initial ratio r=acrylate/N—H of between $r_{inf}$ and 1.1 $r_{sup}$ with the values $r_{inf}$ and $r_{sup}$ being defined according to equations (1) and (2) below:

$$r_{inf}=0.90*(f_A-1)*(f_B-1) \tag{1}$$

$$r_{sup}=2*f_A+2*f_B-6 \tag{2}$$

and with an average number $n_{av}$ of repeating units per oligomer defined according to equation (3) below:

$$n_{av}=1/[(r*f_A/f_B)+1-f_A] \tag{3}$$

2. The oligomer of claim 1, wherein said amine A) bears in addition, at least one tertiary amine function and is selected from: dimethylaminopropylamine (DMAPA), dimethylaminopropylaminopropylamine (DMAPAPA) and 1,4-bis(3-aminopropyl)piperazine (1,4-BAPP) and with a content of nitrogen $t_A$ resulting from the amine of greater than or equal to 0.35 mEq/g.

3. The oligomer of claim 1, wherein the viscosity of said acrylate B) measured according to the ISO 2555 method at 23° C. is less than 200 mPa·s under a shear rate of 100 s$^{-1}$.

4. The oligomer of claim 1, wherein said acrylate B) is selected from the group consisting of: b1) optionally alkoxylated aliphatic or cycloaliphatic polyol acrylates, b2) oligoether acrylates, b3) alkoxylated phenolic acrylates and b4) acrylated aminoacrylates and mixtures thereof.

5. The oligomer of claim 1, wherein said amine A) is selected from the group consisting of: a1) an aliphatic amine, a2) a cycloaliphatic amine and a3) an aralkylene amine with the amine function at a position other than the alpha or beta position of the aromatic ring, and mixtures thereof.

6. The oligomer of claim 1, wherein said functionalities $f_A$ and $f_B$ are selected so that the sum $f_A+f_B$ does not exceed 8.

7. The oligomer of claim 1, wherein the oligomer has a content of acrylate groups $t_{acr}$ of greater than 2.3 mmol/g or milliequivalents/g.

8. The oligomer of claim 1, wherein the oligomer has a number-average molecular mass Mn defined according to equation (4) below, ranging from 275 to 5000:

$$M_n=M_B+(n_{av}*M_u) \tag{4}$$

with $M_u$ being the molar mass of the repeating unit defined according to equation (5) below:

$$M_u=M_A+(f_{A2}+2*f_{A1}-1)*M_B \tag{5}$$

$n_{av}$ being the average number of repeating units as defined in claim 1, $M_B$ being the molar mass of the acrylate B), $M_A$ being the molar mass of the amine A), $f_{A1}$ being the number of primary amine —$NH_2$ functions, per amine A) and $f_{A2}$ being the number of secondary amine —NH— functions, per amine A).

9. The oligomer of claim 1, wherein the oligomer has a content of nitrogen $t_A$ resulting from the amine expressed in mEq/g ranging from 0.4 to 5 with $t_A$ being defined according to equation (6) below:

$$t_A=1000*n_{av}*(f_{A1}+f_{A2}+f_{A3})/Mn \tag{6}$$

with Mn being the number-average molecular mass as defined as claimed in claim 8, $f_{A1}$ being the number of primary amine —$NH_2$ functions, per amine A) and $f_{A2}$ being the number of secondary amine —NH— functions, per amine A)

$f_{A3}$ being the number of tertiary amine —N=functions, per amine A).

10. The oligomer of claim 1, wherein said amine A) has a functionality $f_A$ greater than or equal to 2 and said acrylate B) has a functionality $f_B$ greater than or equal to 3 or conversely said amine A) has a functionality $f_A$ greater than or equal to 3 and that said acrylate B) has a functionality $f_B$ greater than or equal to 2.

11. The oligomer of claim 1, wherein:

said amine A) is of general formula $(NH_2)_{fA1}R2(NHR3)_{fA2}$, with R2=R'(NR"R''')$_{fA3}$, R3, R', R" and R''' being identical or different $C_1$ to $C_3$ alkyls with $f_{A1}$ being equal to 0 and being the number of primary amine functions per mole, $f_{A2}$ being greater than or equal to 2 and being the number of secondary amine functions per mole and $f_{A3}$ being greater than 0 and being the number of tertiary amine functions per mole and with $f_A=f_{A2}$ said acrylate B) is of general formula $R1(X)_{fB}$ with X being a $CH_2$=CH—$CO_2$— acrylate group and R1 being the residue of said acrylate B) bearing $f_B$ acrylates per mole said oligomer comprises the product of the general formula (I) below:

$$X_{(fB-1)}R1[O_2CCH_2CH_2NR3R2Y_{(fA2-2)}NR3CH_2CH_2CO_2R1X_{(fB-2)}]_nX \tag{I}$$

with Y=—(NR3$CH_2CH_2$COOR1$X_{(fB-1)}$).

12. The oligomer of claim 1, wherein:
said amine A) is of general formula $(NH_2)_{f_{A1}}$ $R2(NHR3)_{f_{A2}}$, with $R2=R'(NR''R''')_{f_{A3}}$, R3, R', R'' and R''' being identical or different $C_1$ to $C_3$ alkyls with $f_{A1}$ being greater than or equal to 1 and being the number of primary amine functions per mole, $f_{A2}$ being greater than or equal to 0 and being the number of secondary amine functions per mole and $f_{A3}$ being greater than 0 and being the number of tertiary amine functions per mole and with

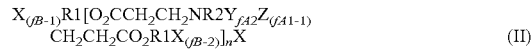

said acrylate B) is of general formula $R1(X)_{f_B}$ with X being a $CH_2=CH-CO_2-$ acrylate group and R1 being the residue of said acrylate B) bearing $f_B$ acrylates per mole
said oligomer comprises the product of the general formula (II) below:

$$X_{(f_{B-1})}R1[O_2CCH_2CH_2NR2Y_{f_{A2}}Z_{(f_{A1}-1)}$$
$$CH_2CH_2CO_2R1X_{(f_{B-2})}]_nX \qquad (II)$$

with $Y=-(NR3CH_2CH_2CO_2R1X_{(f_{B-1})}$ and
$Z=-(N(CH_2CH_2COOR1X_{(f_{B-1})})_2)$.

13. The oligomer of claim 10, wherein said functionality $f_A$ is equal to 3 and said amine A) is selected from a diamine bearing a primary amine function and a secondary amine function or a triamine bearing 3 secondary amine functions.

14. The oligomer of claim 10, wherein said amine A) has a functionality $f_A$ equal to 2 and is a primary amine or a diamine bearing 2 secondary amine functions and that said acrylate B) is an optionally alkoxylated triacrylate with, in the case where said triacrylate is alkoxylated, a number of alkoxy units per acrylate that does not exceed 3 if said alkoxy is ethoxy and a number of alkoxy units per acrylate that does not exceed 1 if said alkoxy is propoxy.

15. The oligomer of claim 10, wherein said amine A) has a functionality $f_A$ equal to 3, which is a primary-secondary diamine or a triamine bearing 3 secondary amine functions and said acrylate B) is an optionally alkoxylated diacrylate with, in the case where said diacrylate is alkoxylated, a number of alkoxy units per acrylate that does not exceed 2 if said alkoxy is ethoxy and a number of alkoxy units per acrylate that does not exceed 1 if said alkoxy is propoxy.

16. The oligomer of claim 10, wherein said functionality $f_A$ is equal to 4 and said amine A) is selected from a diamine bearing 2 primary amine functions or a triamine bearing 1 primary amine function and 2 secondary amine functions or a tetra-amine bearing 4 secondary amine functions.

17. The oligomer of claim 10, wherein said functionality $f_A$ is equal to 5 and said amine A) is selected from a triamine bearing two primary amine functions and one secondary amine function or a tetra-amine bearing one primary amine function and three secondary amine functions or a penta-amine bearing 5 secondary amine functions.

18. The oligomer of claim 10, wherein said functionality $f_A$ is equal to 6 and said amine A) is selected from a triamine bearing three primary amine functions or a tetra-amine bearing 2 primary amine functions and 2 secondary amine functions or a penta-amine bearing 1 primary amine function and 4 secondary amine functions or a hexa-amine bearing 6 secondary amine functions.

19. The oligomer of claim 1, wherein the oligomer results from the reaction between at least two amines A) and/or at least two acrylates B).

20. The oligomer of claim 1, wherein it comprises n repeating units with a molecular distribution as a function of n comprising at least the 4 products corresponding to: n=0 and n=1 and n=2 and n=3 and with at least 50% by weight of said distribution corresponding to n less than or equal to 3.

21. A process for preparing an oligomer as defined in claim 1, comprising a step of Michael polyaddition reaction of said at least one amine A) to said at least one acrylate B), in the presence of a radical polymerization inhibitor and in the absence of any solvent, of any catalyst and of any other reactant except for said amine A) and said acrylate B) and said inhibitor, said process comprising the gradual and continuous addition of said amine A) to said acrylate B) already present in the reactor and always in stoichiometric excess and with said reaction taking place at a temperature above 40° C. and below 90° C., and with said reaction being stopped at a degree of conversion of the N—H amine functions of at least 95% and with an initial ratio r of acrylate functions to N—H amine functions, r=acrylate/N—H being between $r_{inf}$ and 1.1 $r_{sup}$ with the values $r_{inf}$ and $r_{sup}$ being defined according to equations (1) and (2) below:

$$r_{inf}=0.90*(f_A-1)*(f_B-1) \qquad (1)$$

$$r_{sup}=2*f_A+2*f_B-6 \qquad (2).$$

22. A crosslinkable composition comprising at least one oligomer as defined in claim 1, with optionally the presence of a reactive diluent.

23. The composition of claim 22, wherein the composition is a radiation-crosslinkable composition which is a coating composition, or is a composition for 3D articles made by superposition of successive layers or is a molding composition.

24. The composition of claim 22, wherein the composition is a peroxide-crosslinkable composition which is a coating composition, or is a chemical sealing composition or is a molding composition.

25. A crosslinked final product wherein the product is obtained by exposing the crosslinkable composition of claim 22 to radiation.

* * * * *